US012657477B2

(12) United States Patent
Wee et al.

(10) Patent No.: US 12,657,477 B2
(45) Date of Patent: *Jun. 16, 2026

(54) ONLINE PROBABILISTIC INVERSE OPTIMIZATION SYSTEM, ONLINE PROBABILISTIC INVERSE OPTIMIZATION METHOD, AND ONLINE PROBABILISTIC INVERSE OPTIMIZATION PROGRAM

(71) Applicant: NEC CORPORATION, Tokyo (JP)

(72) Inventors: Wemer Wee, Tokyo (JP); Yasuhisa Suzuki, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/360,129

(22) Filed: Jul. 27, 2023

(65) Prior Publication Data

US 2023/0368040 A1    Nov. 16, 2023

Related U.S. Application Data

(63) Continuation of application No. 17/286,866, filed as application No. PCT/JP2018/039612 on Oct. 25, 2018, now Pat. No. 12,524,682.

(51) Int. Cl.
| | |
|---|---|
| *G06N 5/01* | (2023.01) |
| *G06N 20/00* | (2019.01) |
| *G06Q 10/0631* | (2023.01) |
| *G16H 40/20* | (2018.01) |

(52) U.S. Cl.
CPC .............. *G06N 5/01* (2023.01); *G06N 20/00* (2019.01); *G06Q 10/063112* (2013.01); *G16H 40/20* (2018.01)

(58) Field of Classification Search
CPC .......... G06N 5/01; G06N 20/00; G16H 40/20; G06Q 10/063112
USPC ......................................................... 706/12
See application file for complete search history.

(56) References Cited

U.S. PATENT DOCUMENTS

| | | | |
|---|---|---|---|
| 6,754,588 | B2 | 6/2004 | Cross et al. |
| 9,155,908 | B2 | 10/2015 | Meltsner et al. |
| 2014/0206926 | A1* | 7/2014 | van der Laarse .... A61N 5/1031 |
| | | | 600/8 |

OTHER PUBLICATIONS

Dong, et al., "Generalized Inverse Optimization through Online Learning", 32nd Conference on Neural Information Processing Systems (NeuIPS 2018), Canada, 2018 (Year: 2018).*
International Search Report for PCT Application No. PCT/JP2018/039612, mailed on Jan. 22, 2019.
Written Opinion for PCT Application No. PCT/JP2018/039612, mailed on Jan. 22, 2019.

(Continued)

*Primary Examiner* — Tsu-Chang Lee
(74) *Attorney, Agent, or Firm* — Sughrue Mion, PLLC

(57) ABSTRACT

An online probabilistic inverse optimization system 10 is proposed for inferring objectives and constraints in an online fashion from changing problem data and corresponding agent decisions. The online probabilistic inverse optimization system 10 includes: a computing unit 11 which computes optimal solutions or decisions based on the forward optimization problem using the problem data that may include objectives, constraints and parameters; and a solving unit 12 which solves the inverse optimization problem using the agent decisions.

5 Claims, 4 Drawing Sheets

(56) References Cited

OTHER PUBLICATIONS

Andreas Barmann et al., "Emulating the expert: Inverse optimization through online learning", In Proceedings of the 34th International Conference on Machine Learning, 2017, pp. 400-410.

Chan, Joyce Yin Tung, "Understanding nurses' preferences to improve scheduling optimization models for chemotherapy clinics", M.Eng. Project Report, Department of Mechanical and Industrial Engineering University of Toronto, May 12, 2011, pp. 1-48, <URL:https://tspace.library.utoronto.ca/bitstream/1807/27212/1/Joyce%20Chan.pdf>.

* cited by examiner

ONLINE PROBABILISTIC INVERSE OPTIMIZATION SYSTEM, ONLINE PROBABILISTIC INVERSE OPTIMIZATION METHOD, AND ONLINE PROBABILISTIC INVERSE OPTIMIZATION PROGRAM

CROSS-REFERENCE TO RELATED APPLICATIONS

The present application is a continuation application of U.S. patent application Ser. No. 17/286,866 filed on Apr. 20, 2021, which is a national stage application of International Application No. PCT/JP2018/039612 filed on Oct. 25, 2018, the disclosures of each of which are hereby incorporated by reference in their entirety.

TECHNICAL FIELD

The present invention relates to an online probabilistic inverse optimization system, an online probabilistic inverse optimization method, and an online probabilistic inverse optimization program.

BACKGROUND ART

In many decision-making systems, an agent faced with complex problems can demonstrate sophisticated behavior and generate solutions which can be considered optimal or expert-level in a certain sense. The possibly multiple and conflicting objectives that the agent considered in order to arrive at an optimal decision or solution are in general very hard to explicitly state and explain. Despite this, it is highly desired to know what the specific objectives were considered, as they can be used in many practical purposes such as the imitation or automation of expert-level decision-making. Inverse optimization is a technique for recovering the objectives of the agent given observations of the agent's optimal decisions or solutions.

Some examples of how inverse optimization is used in practice are described in PTL1 and PTL2. PTL1 employed inverse optimization for finding the parameters for radio-therapy treatment planning that will satisfy user-entered treatment objective criteria. PTL2 used inverse optimization for modifying the input parameters to a forward model, which is used for predicting attributes related to stratigraphy, to achieve a closer match between predicted attribute and observed attribute. In both of the examples above, as is in other standard applications of inverse optimization, the observations of the desired outcomes and the corresponding agent decisions applied are given at the start of the inverse optimization process, and then an objective function, which might contain several terms, or the parameters or weights involved in the objective function, are obtained as a result.

A common situation in many practical applications is that the optimization problem can have or depend on data or parameters which are time-varying. In this sense, the optimization problem is said to change online, and the agent derives an optimal solution that is dependent on how the problem changes over time. Most of the existing inverse optimization techniques do not disclose how to deal with such problems, and only recently has this problem gained attention. NPL1 describes a technique for recovering linear objectives in an online manner given problem input data and the agent's corresponding decisions over time.

As a motivating example, consider employee scheduling such as nurse shift assignment systems. An expert hospital manager may be given the main objectives of minimizing total hospital cost and minimizing inefficiencies resulting from a specific assignment. Aside from the main objectives, there are several hard constraints and soft constraints in the system such as having a maximum number of hours per day for each nurse, a set minimum number of days per week, all patients having at least one nurse assigned, personal preferences of nurses, manager preferences for matching skill level of nurses to patients' situations and doctors' situations, and so on. In addition, the objectives and constraints can all change over time and have some parameters that affect them such as seasons, events or number of patients. This problem can become very complex as the number of nurses increase, and the characterization of an optimal schedule or nurse assignment changes with respect to the parameters of the problem or hospital situation. It is thus very important to be able to learn the objectives and constraints of an expert manager in an online fashion from observations of the different circumstances encountered and the corresponding nurse assignments created in order to fully automate the process with the resulting schedules generated resembling the expert manager's expected decisions.

CITATION LIST

Patent Literature

[PTL 1]
  U.S. Pat. No. 9,155,908
[PTL 2]
  U.S. Pat. No. 6,754,588

Non Patent Literature

[NPL 1]
  Andreas Barmann, Sebastian Pokutta, and Oskar Schneider, "Emulating the expert: Inverse optimization through online learning," In Proceedings of the 34th International Conference on Machine Learning, pages 400-410, 2017.

SUMMARY OF INVENTION

Technical Problem

A main difference of online inverse optimization from the standard, or forward, optimization problem is that since the underlying problem is changing, a more appropriate model of the objectives of the agent should adapt to the changes as well. Furthermore, the possible temporal dependencies of the optimal solutions should also be taken into account.

In addition to the issue of time-varying forward problems, the recovery of the constraints involved in the optimization problems is not covered by the existing works. Learning the constraints or their relative importance to the standard objectives is very important in many safety-critical applications, and the simultaneous recovery of such information together with the objectives is very valuable for deployment in practice.

In prior works, which are mostly offline inverse optimization techniques, the recovery of objectives is based on optimization theoretic approaches such as Karush-Kuhn-Tucker (KKT) system decomposition and dualization, which may not be the best approach to handling probabilistic issues such as those related to the quality of problem data and agent decisions. At the same time, for example in NPL1, the objectives considered are mostly linear in form, and there are some restrictions on objective weights that make it difficult to learn conflicts and importance of different objectives.

To create a more unified approach to handling the learning of the objectives and constraints in an online fashion given changing problem data and agent decisions, or dealing with data quality issues such as noisy measurements or suboptimality of solutions or decisions, an online probabilistic machine learning approach to inverse optimization is desired.

The subject matter of the present invention is directed to realizing the above features in order to overcome, or at least reduce the effects of, one or more of the problems set forth above.

One of the objects of the present invention is to provide an online probabilistic inverse optimization system, an online probabilistic inverse optimization method, and an online probabilistic inverse optimization program that are capable of learning the objectives and constraints in an online fashion given changing problem data or streaming problem data and corresponding agent decisions over time.

Solution to Problem

An online probabilistic inverse optimization system according to the present invention is an online probabilistic inverse optimization system which infers objectives and constraints in an online fashion from changing problem data and corresponding agent decisions, the online probabilistic inverse optimization system includes: a computing unit which computes optimal solutions or decisions based on the forward optimization problem using the problem data that may include objectives, constraints and parameters; and a solving unit which solves the inverse optimization problem using the agent decisions.

An online probabilistic inverse optimization method according to the present invention is an online probabilistic inverse optimization method which infers objectives and constraints in an online fashion from changing problem data and corresponding agent decisions, the online probabilistic inverse optimization method includes: computing optimal solutions or decisions based on the forward optimization problem using the problem data that may include objectives, constraints and parameters; solving the inverse optimization problem using the agent decisions.

An online probabilistic inverse optimization program according to the present invention is an online probabilistic inverse optimization program mounted on a computer which infers objectives and constraints in an online fashion from changing problem data and corresponding agent decisions, the program causing the computer to perform: a computation process of computing optimal solutions or decisions based on the forward optimization problem using the problem data that may include objectives, constraints and parameters; and a solving process of solving the inverse optimization problem using the agent decisions.

Advantageous Effects of Invention

According to the present invention, it is possible to learn the objectives and constraints in an online fashion given changing problem data or streaming problem data and corresponding agent decisions over time.

DESCRIPTION OF EMBODIMENTS

Figure 1:
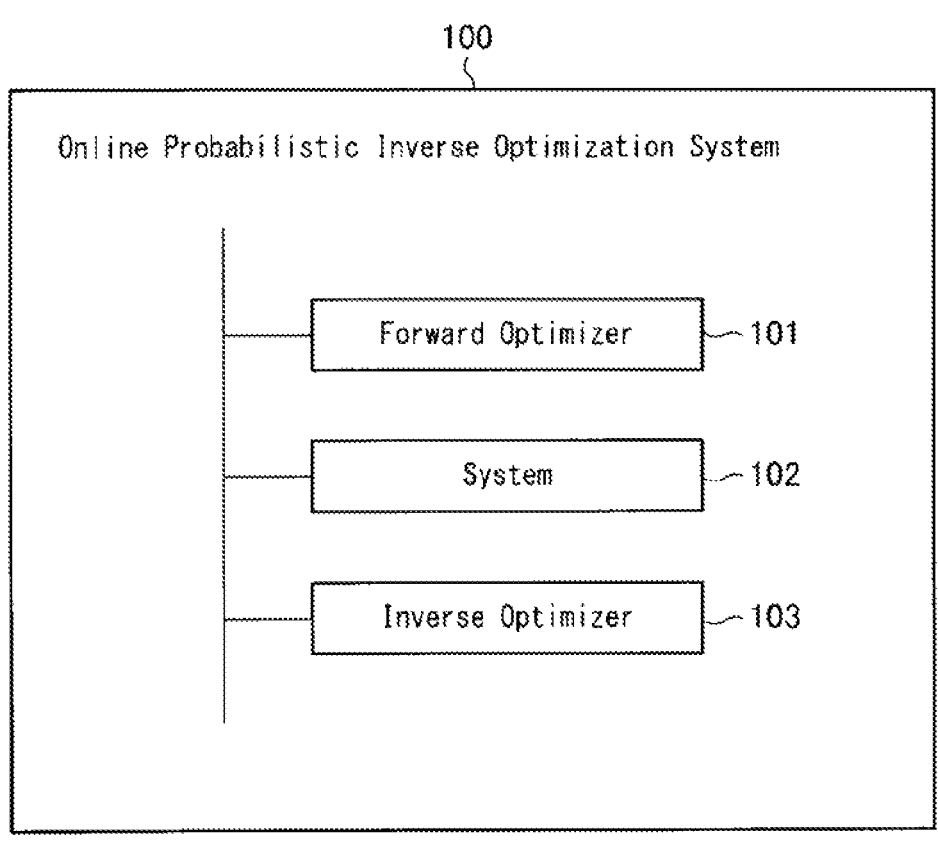
FIG. 1 is a block diagram showing an example of a structure of an online probabilistic inverse optimization system 100 according to a first exemplary embodiment of the present invention.

The present invention infers objectives and constraints in an online fashion from changing problem data or streaming problem data and corresponding agent decisions, which can be used in a forward optimization solver for computing optimal decisions or solutions that are similar to the agent's decisions in terms of certain similarity measures.

By employing machine learning techniques, the learning of the objectives and constraints in an online manner can be performed under a probabilistic framework. As a machine learning-based solution, the approach is expected to be more effective as larger amounts of training data involving problem or parameter information and corresponding agent decisions can be collected for the different tasks. The objectives and constraints are improved by providing feedback or corrections to the corresponding decisions that can be generated.

Using the proposed invention, the possibly time-dependent intention or parameter-dependent intention of agents can be captured by recovering or learning objectives and constraints in an online fashion from changing problem data and corresponding agent decisions. The objectives and constraints inferred may then be used to explain observed decisions, describe the intent of the agent, and improve the design of the forward optimizer to achieve imitation and automation of a similar level of decision-making capability.

A machine learning approach allows us to employ probabilistic methods where the online inverse optimization problem can be treated as a maximum likelihood problem, which allows the characterization of the observed agent decisions in a probabilistic manner. At the same time, this approach is flexible enough to allow the consideration of optimization theoretic measures such as those based on KKT and dualization concepts.

The present invention is different from prior arts like PTL 1 and PTL 2 due to the online setting being considered, where the problem changes over time and the corresponding agent decisions are affected by such changes. The intention of the agent is thus assumed to adapt to the changes as well. Although NPL 1 deals with online inverse optimization, the present invention can handle the constraints as part of the learning process. Moreover, compared to the prior arts, no restrictions on the structure of the objectives and constraints are assumed. The proposed probabilistic formulation can also be employed to leverage the use of statistical concepts for dealing with notions related to data and decision quality.

The following describes an exemplary embodiment of the present invention with reference to drawings. The present invention relates to a method and system for online probabilistic inverse optimization, i.e., learning objectives and constraints in an online fashion from changing problem data and corresponding agent decisions for use in a forward optimization solver. The preferred and alternative embodiments, and other aspects of the subject matter of the present disclosure will be best understood with reference to a detailed description of specific embodiments, which follows, when read in conjunction with the accompanying drawings.

The following discussion of the embodiments of the present disclosure directed to a method and system for online probabilistic inverse optimization is merely exemplary in nature, and is in no way intended to limit the disclosure or its applications or uses.

First Exemplary Embodiment

Figure 2:
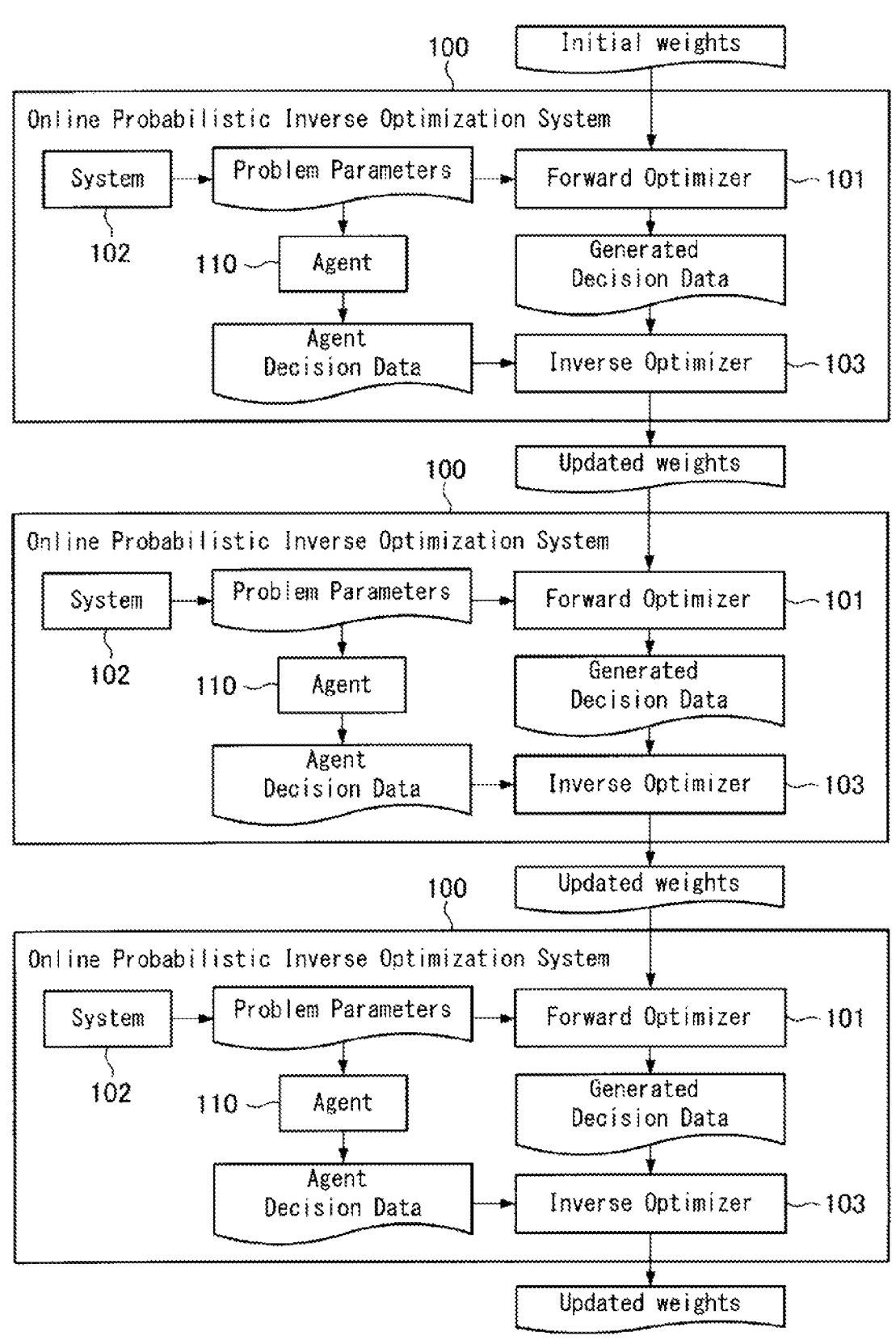
FIG. 2 is an explanatory diagram showing an example of an operation of the online probabilistic inverse optimization system 100 according to the first exemplary embodiment of the present invention.

FIG. 1 is a block diagram showing an example of a structure of an online probabilistic inverse optimization system 100 according to a first exemplary embodiment of the present invention. Moreover, FIG. 2 is an explanatory diagram showing an example of an operation of the online probabilistic inverse optimization system 100 according to the first exemplary embodiment of the present invention. The online probabilistic inverse optimization system 100 of the present embodiment infers the objective weights and constraints in an online fashion from changing problem data and agent decisions for use in a forward optimizer to imitate agent decisions and generalize the agent's intent in different settings.

The online probabilistic inverse optimization system 100 according to the present exemplary embodiment includes a forward optimizer 101, a system 102 to be optimized, and an inverse optimizer 103. The system 102, in general, has one or several observable parameters or observable signals, which can affect the variables to be optimized, or can be directly used in a performance metric for measuring the quality of the decisions to be computed or applied by an agent or the forward optimizer 101.

According to the present exemplary embodiment, at each time instant, the system 102 gives some observable parameters or measurable parameters which quantities to be optimized may depend on. Based on the problem data or problem parameters, the forward optimizer 101 can compute optimal decisions("Generated Decision Data" shown in FIG. 2) on the basis of objectives and constraints that have been initialized("Initial weights" shown in FIG. 2), or learned from the inverse optimizer 103. On the other hand, an agent 110 may have computed agent decisions("Agent Decision Data" shown in FIG. 2) on the basis of the problem data if using historical training data for learning, or can compute agent decisions if performing online learning. The agent decisions are used in the inverse optimizer 103 for updating the objectives and constraints. The learned objectives and constraints or updated objectives and constraints("Updated weights" shown in FIG. 2) are then sent to the forward optimizer 101 for use in the next iteration or time step.

The online probabilistic inverse optimization system 100 of the present invention can be applied to employee scheduling systems, such as a nurse shift assignment system. Therefore, the online probabilistic inverse optimization system 100 of the present embodiment can be referred to as an online employee scheduling system. In this context, the forward optimizer 101 computes decisions or employee task assignments for generating an optimal schedule given changing situation parameters and constraints.

The outputs of system 102 can be problem observations, measurements or parameters related to the variables or quantities being optimized in the forward optimizer 101. The outputs of the forward optimizer 101 are optimal decisions needed to be applied in order to reach certain objectives while satisfying constraints. The outputs of the inverse optimizer 103 are the objectives and constraints, or their relative importance, that specifically encodes what it is that needs to be optimized. In the employee scheduling example, the problem data from the system 102 can be the total number of working hours for all employees and the total number of tasks or customers for a specific time period, the forward optimizer 101, on the basis of initialized objectives and constraints or current objectives and constraints, can compute the scheduling or assignment decisions containing the number of working hours and specific tasks assigned to each employee, and the inverse optimizer 103 can output the relative importance between the cost of employee shifts to the company, the customer constraints, and the employee preferences.

The forward optimizer 101 solves an optimization problem composed of an objective function, a set of constraints and a set of associated parameters. The objective function may contain one or several terms or features that relate to different performance metrics that are used to measure the quality of a decision in relation to the system 102. The objective function can be accompanied by input and outputs constraints, and the constrained optimization problem is solved to find decisions that are optimal in the sense of the given performance metrics and satisfying the constraints.

As a simple case, the objective function in the forward optimizer 101 can be a weighted sum of terms or features that may be chosen manually or generated automatically from data. Similarly, the constraints are also composed of features which can be generated manually or automatically. In the nurse shift assignment example, some possible objective features can be the cost to the hospital of a chosen schedule, or the effect of a shift assignment to the satisfaction of patients, doctors and nurses. Hard constraints can include features such as number of nurses for each patient, minimum number of days of service per week for the nurses, and maximum number of hours per shift for each nurse. Soft constrains may include the preferences of the managers, the implicit skill level matching of nurses to level of complexity of a patient's condition, and the personal preferences of the nurses.

The inverse optimizer 103 works as an updater for the objectives and constraints, with the updating methods based on machine learning techniques. In particular, the inverse optimizer 103 treats the inverse optimization problem as an online machine learning problem, formulated as a maximum likelihood estimation problem. A likelihood function is chosen to characterize the distribution of the agent decisions, and the appropriate weights or parameters of the objectives and constraints are then the solutions maximizing the likelihood of the observed agent decisions. Aside from the freedom in choosing the criterion or distribution of the observed data, regularization and other constraints can also be added. For example, it is possible to enforce a constraint that the features of the generated solution or the generated decision should match the features of the agent's decision. The update mechanism may then involve the difference between the feature of the generated decision and the feature of actual agent decision. Constraints based on KKT or duality gap conditions can similarly be imposed in order to characterize the appropriate objectives and constraints in further detail. By employing a Lagrange relaxation approach, the constraints or their relative importances or prioritization together with the objectives can be learned from the solution of an extended structure for the objective in the maximum likelihood formulation.

By design, the proposed approach uses a probabilistic criterion for inverse optimization without the need for any restrictions on the parameters of the objectives and constraints. Moreover, the objectives and constraints are learned simultaneously in an online manner. Due to the flexibility of the approach, it is possible to outperform existing methods on the basis of different performance metrics.

As the initial weights for the objectives and constraints, it is possible to use random initialization or to apply the standard inverse optimization technique to agent decision data if available. Note that as an online learning algorithm, the online probabilistic inverse optimization algorithm proposed can also be applied to the standard inverse optimization scenario, wherein the method is applied to a historical collection of problem data and corresponding agent decisions, with the advantage of being more efficient in terms of learning when the number of agent decisions and problem data is large.

The updating of objectives and constraints will continue as long as new problem data and agent decision can be observed. In this sense, as long as the agent provides a solution or corrections to the solution generated by the forward optimizer 101, the learning process is continued until convergence in terms of some performance metric is achieved.

Aside from the usual case of computing the updates for the objectives and constraints at each time using the latest samples of problem data and corresponding agent decision, it is also possible to employ a sliding window or mini-batch approach to use a certain number of recent samples from the current instance. This can potentially speed up the convergence of the online inverse optimization learning process.

The forward optimizer 101 and the inverse optimizer 103 are each implemented by a CPU (Central Processing Unit) of a computer that operates in accordance with a program (inverse optimization program). For example, the program may be stored in a storage unit (not shown) included in the online probabilistic inverse optimization system 100, and the CPU may read the program and operate as the forward optimizer 101 and the inverse optimizer 103 in accordance with the program.

In the online probabilistic inverse optimization system 100 of the present embodiment, the forward optimizer 101 and the inverse optimizer 103 may each be implemented by dedicated hardware. Further, the online probabilistic inverse optimization system 100 according to the present embodiment may be configured with two or more physically separate devices which are connected in a wired or wireless manner.

Figure 3:
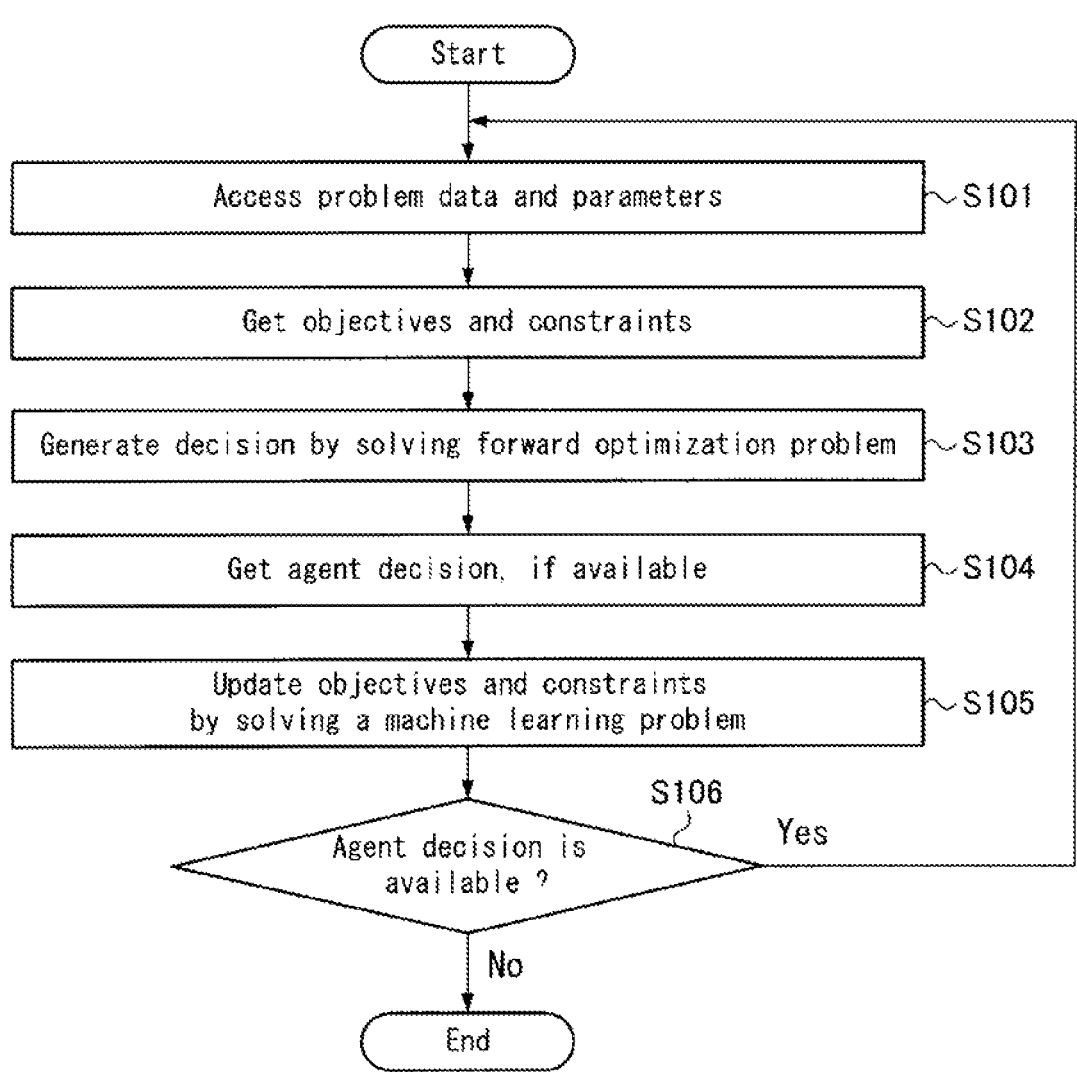
FIG. 3 is a flowchart showing an example of the operation of the online probabilistic inverse optimization system 100 according to the first exemplary embodiment of the present invention.

The following describes an example of the operation of the online probabilistic inverse optimization system 100 in this exemplary embodiment. FIG. 3 is a flowchart showing an example of the operation of the online probabilistic inverse optimization system 100 according to the first exemplary embodiment of the present invention.

In Step S101, the problem data or the problem parameters are obtained from the system 102. This step is done every time step or iteration.

In Step S102, the objectives and constraints are obtained via initialization, if at the first step of the process, by application of a batch inverse optimization technique on historical training data, if available, or using the previously updated objectives and updated weights, if the intermediate part of the learning process.

In Step S103, using the problem parameters, the objectives and constraints, the forward optimizer 101 computes the optimal decision by solving a constrained optimization problem.

In Step S104, the agent decision corresponding to the problem parameters are accessed, if available.

In Step S105, using the agent decision and the optimal decision generated in Step S103, an online machine learning problem is solved in the inverse optimizer 103 to compute for the updated objectives and constraints.

If the agent decision is available (Yes in Step S106), the online probabilistic inverse optimization system 100 performs the processing of Step S101 again. If the agent decision is not available (No in Step S106), the online probabilistic inverse optimization system 100 ends the operation shown in FIG. 3.

In this manner, in the present exemplary embodiment, the forward optimizer 101 generates decisions using objectives and constraints that may depend on or be affected by data or parameters from system 102, and the inverse optimizer 103 uses the agent decisions and generated decisions in an online machine learning formulation for updating the objectives and constraints.

With the above structure, the learning of objectives and constraints from problem data and corresponding agent decisions in an online fashion can be realized. The learned objectives and constraints can be used for imitating and automating the decision-making abilities of an agent, and the dependencies of the agent's intentions on the changing nature of the problem are taken into account. That is, according to the present invention, objectives and constraints learned using the online probabilistic inverse optimization method can be used in a forward optimizer for computing decisions that match the agent's decisions in terms of features and level of expectation.

Consider the case of nurse shift assignment, in which a forward optimizer can be employed to generate the schedules or assignments for the entire nursing staff. Depending on the date, time, season and certain events, a hospital manager may need to create a good schedule that meets several general targets or objectives for the hospital and balances many different hard constraints and soft constraints. For a small number of factors and number of nurses, the staff assignment problem is fairly easy to solve. In practice however, the number of external factors and staff can be large. In addition, the hospital manager needs to take into account many implicit objectives and constraints that are difficult to explicitly state.

To avoid manual tuning and to automatically capture the possibly time-varying nature and parameter-varying nature of the intentions of the hospital manager, the present invention proposes to use the hospital problem data and corresponding nurse assignments to learn the objectives and constraints of the manager in an online manner or sequential manner for the purpose of adjusting a forward optimizer for automating the complex decision making required to generate a good schedule.

The hospital problem data may include information such as the number of patients, seasonality of certain conditions, the physical state of the patients and so on. The hospital manager decision includes the specific patients, shifts and number of hours assigned to each nurse. The shifts may depend on a number of factors in the hospital such as those mentioned above.

The forward optimizer or scheduler requires the objectives and constraints which can be chosen manually on the basis of quantities of interest to the hospital, such as the resulting cost of a particular shift assignment to the hospital, or the satisfaction of the patients, doctors of nurses based on the generated schedule. Hard constraints may relate to the allowable maximum shift and minimum shift for each nurse.

Some features for soft constraints may include skills and compatibility of each nurse to a specific patient condition and other staff in the same shift. Other features can also be designed manually or built automatically from the assignment data to obtain a more detailed characterization of a certain schedule or assignment for the entire nursing staff.

At the start of the learning process, the weights for the objectives and constraints may be randomly initialized, and the forward optimizer generates a schedule or shift assignment that is optimal in the sense of the features used in the objectives and constraints and their relative importance. The resulting schedule and the schedule created by the hospital manager can then be used in the inverse optimizer for measuring similarity or deviation and updating the objectives and constraints. This process is continued until more samples of the hospital manager's schedules are available or until convergence is achieved.

Figure 4:
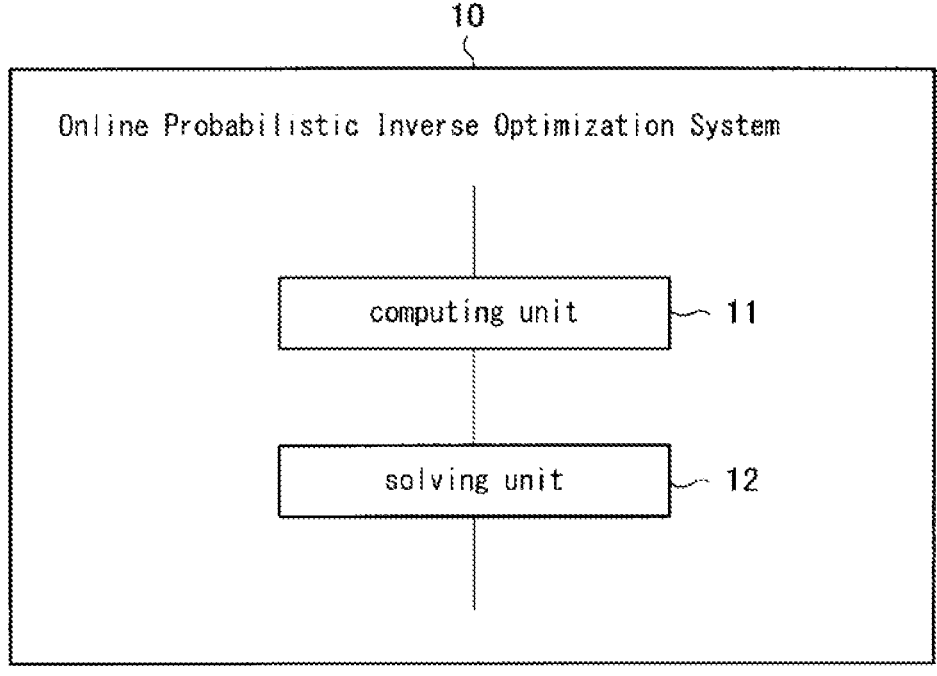
FIG. 4 is a block diagram showing an outline of an online probabilistic inverse optimization system according to the present invention.

An outline of the present invention will be described below. FIG. 4 is a block diagram showing an outline of an online probabilistic inverse optimization system according to the present invention. An online probabilistic inverse optimization system 10 according to the present invention which infers objectives and constraints in an online fashion from changing problem data and corresponding agent decisions, the online probabilistic inverse optimization system 10 includes: a computing unit 11 (the forward optimizer 101, for example) which computes optimal solutions or decisions based on the forward optimization problem using the problem data that may include objectives, constraints and parameters; and a solving unit 12 (the inverse optimizer 103, for example) which solves the inverse optimization problem using the agent decisions.

With the structure, the online probabilistic inverse optimization system can learn the objectives and constraints in an online fashion given changing problem data or streaming problem data and corresponding agent decisions over time.

Further, the solving unit 12 may measure the similarity or deviation between the solutions of the agent and the computed optimal solutions or decisions by the computing unit 11 using one or more similarity measures.

With the structure, the online probabilistic inverse optimization system can learn the objectives and constraints more effectively.

Further, the solving unit 12 may use online machine learning for maximizing the likelihood of a model given agent decisions for solving the inverse optimization problem.

With the structure, the online probabilistic inverse optimization system can solve the inverse optimization problem more efficiently.

Further, the solving unit 12 may update the objectives and constraints on the basis of the maximum likelihood formulation and the measured similarity or deviation used in the solving unit 12.

With the structure, the online probabilistic inverse optimization system can increase the accuracy of learning.

Further, the solving unit 12 may solve the inverse optimization problem as an extended online maximum likelihood problem employing Lagrange relaxation and duality gap conditions to update the objectives and constraints.

With the structure, the online probabilistic inverse optimization system can learn and update the objectives and constraints in an online fashion given changing problem data and the corresponding solutions or decisions by an agent or several agents displaying some kind of skill or expertise.

The foregoing description of preferred and alternative embodiments is not intended to limit or restrict the scope or applicability of the inventive concepts of the present disclosure. One skilled in the art will readily recognize from such discussion and from the accompanying drawings and claims that various changes, modifications and variations can be made therein without departing from the spirit and scope of the disclosure as defined in the following claims.

REFERENCE SIGNS LIST

10, 100 online probabilistic inverse optimization system
11 computing unit
12 solving unit
101 forward optimizer
102 system
103 inverse optimizer
110 agent

The invention claimed is:

1. An online probabilistic inverse optimization system which infers objectives and constraints in an online fashion from time-varying nurse shift assignment problem data and corresponding hospital manager decisions, the online probabilistic inverse optimization system comprising:

a memory storing computer-executable program code;
a forward optimizer comprising at least one processor, the forward optimizer configured to execute the program code, wherein the program code is configured to, when executed by the at least one processor, cause the forward optimizer to:
retrieve the time-varying nurse shift assignment problem data including objectives, constraints and parameters, the time-varying nurse shift assignment problem data including hospital problem data including a number of patients, seasonality of certain conditions, or a physical state of the patients,
compute an optimal solution or decision by solving a forward optimization problem based on the retrieved time-varying nurse shift assignment problem data, and
output the computed optimal solution; and
an inverse optimizer comprising at least one processor configured to execute the program code, wherein the program code is configured to, when executed by the at least one processor, cause the inverse optimizer to:
retrieve the hospital manager decisions and the computed optimal solution from the forward optimizer,
measure a deviation or similarity between the hospital manager decisions and the computed optimal solution using one or more similarity measures,
solve an inverse optimization problem treated as an online machine learning problem formulated as a maximum likelihood estimation problem, the inverse optimizer maximizing a likelihood of a model given the hospital manager decisions,
further solve the inverse optimization problem as an extended online maximum likelihood problem employing Lagrange relaxation and duality gap conditions to update the objectives and the constraints, and
output updated objective weights and updated constraints for use by the forward optimizer,
wherein the forward optimizer and the inverse optimizer iteratively operate to process new time-varying nurse shift assignment problem data and hospital manager decisions,
wherein the forward optimizer uses the updated objective weights and the updated constraints to compute a new optimal solution that matches or imitates the hospital manager decisions in terms of features of the nurse shift assignment problem and improves an accuracy of learning and an adaptability to changes in the nurse shift assignment problem data.

2. An online probabilistic inverse optimization method which infers objectives and constraints in an online fashion from time-varying nurse shift assignment problem data and corresponding hospital manager decisions, the online probabilistic inverse optimization method comprising:

performing forward optimization, including:

retrieving the time-varying nurse shift assignment problem data including objectives, constraints and parameters, the time-varying nurse shift assignment problem data including hospital problem data including a number of patients, seasonality of certain conditions, or a physical state of the patients, computing an optimal solution or decision by solving a forward optimization problem based on the retrieved time-varying nurse shift assignment problem data, and outputting the computed optimal solution; and performing inverse optimization, including:

retrieving the hospital manager decisions and the computed optimal solution from the forward optimization, measuring a deviation or similarity between the hospital manager decisions and the computed optimal solution using one or more similarity measures, solving an inverse optimization problem treated as an online machine learning problem formulated as a maximum likelihood estimation problem, the inverse optimizer maximizing a likelihood of a model given the hospital manager decisions, and further solving the inverse optimization problem as an extended online maximum likelihood problem employing Lagrange relaxation and duality gap conditions to update the objectives and the constraints, and outputting updated objective weights and updated constraints for use by the forward optimization, wherein the forward optimization and the inverse optimization iteratively operate to process new time-varying nurse shift assignment problem data and hospital manager decisions, and wherein the forward optimization uses the updated objective weights and the updated constraints to compute a new optimal solution that matches or imitates the hospital manager decisions in terms of features of the nurse shift assignment problem and improves an accuracy of learning and an adaptability to changes in the nurse shift assignment problem data.

3. A non-transitory computer-readable capturing medium having captured therein an online probabilistic inverse optimization program mounted on a computer, including at least one processor, which infers objectives and constraints in an online fashion from time-varying nurse shift assignment problem data and corresponding hospital manager decisions, the program causing the at least one processor to perform:

forward optimization processing, including:

data retrieving processing including retrieving the time-varying nurse shift assignment problem data including objectives, constraints and parameters, the time-varying nurse shift assignment problem data including hospital problem data including a number of patients, seasonality of certain conditions, or a physical state of the patients, solution computing processing including computing an optimal solution or decision by solving a forward optimization problem based on the retrieved time-varying nurse shift assignment problem data, and output processing including outputting the computed optimal solution; and inverse optimization processing, including:

decision retrieving processing including retrieving the hospital manager decisions and the computed optimal solution from the forward optimization, measurement processing including measuring a deviation or similarity between the hospital manager decisions and the computed optimal solution using one or more similarity measures, optimization solving processing including solving an inverse optimization problem treated as an online machine learning problem formulated as a maximum likelihood estimation problem, the inverse optimizer maximizing a likelihood of a model given the hospital manager decisions, further solving the inverse optimization problem as an extended online maximum likelihood problem employing Lagrange relaxation and duality gap conditions to update the objectives and the constraints, and weight output processing including outputting updated objective weights and updated constraints for use by the forward optimization, wherein the forward optimization processing and the inverse optimization processing iteratively operate to process new time-varying nurse shift assignment problem data and hospital manager decisions, and wherein the forward optimization uses the updated objective weights and the updated constraints to compute a new optimal solution that matches or imitates the hospital manager decisions in terms of features of the nurse shift assignment problem and improves an accuracy of learning and an adaptability to changes in the nurse shift assignment problem data.

4. The online probabilistic inverse optimization system according to claim 1, wherein:

the forward optimizer and the inverse optimizer are interconnected;

the forward optimizer computes optimal solutions at least two times;

the inverse optimizer solves the inverse optimization problem at least two times;

solving the inverse optimization problem outputs a set of updated weights; and during the second and later computation of the optimal solution, the forward optimizer inputs the updated weights from the inverse optimizer, and utilizes the updated weights in computing the optimal solution.

5. The online probabilistic inverse optimization system according to claim 1, wherein the online probabilistic inverse optimization system is configured to imitate and automate a decision-making ability of the hospital manager by using the updated objective weights and the updated constraints to compute decisions that match or imitate the hospital manager decisions in terms of features and level of expectation.

* * * * *